United States Patent [19]

Cragoe, Jr. et al.

[11] 4,298,743
[45] Nov. 3, 1981

[54] 4-(SUBSTITUTED PHENYL THIAZOLYL)-3-HYDROXY-3-PYRROLINE-2,5-DIONES

[75] Inventors: Edward J. Cragoe, Jr., Lansdale; Clarence S. Rooney, Worcester, both of Pa.; Haydn W. R. Williams, Dollard des Ormeaux, Canada

[73] Assignee: Merck & Co., Inc., Rahway, N.J.

[21] Appl. No.: 74,465

[22] Filed: Sep. 11, 1979

[51] Int. Cl.$^3$ ............... C07D 417/04; A61K 31/425
[52] U.S. Cl. .................................. 548/203; 424/270
[58] Field of Search ................ 548/203, 202; 424/270

[56] References Cited

U.S. PATENT DOCUMENTS

| | | | |
|---|---|---|---|
| 3,074,954 | 1/1963 | Landquist | 548/205 |
| 3,340,263 | 9/1967 | Stachelln et al. | 544/372 |
| 3,528,980 | 9/1970 | Islip | 424/270 |

OTHER PUBLICATIONS

Liao et al., Arch. Biochem. Biophys., 154, pp. 68–75 (1973).
Harlay, J. Pharm. Chim., 24, pp. 537–548 (1936).
Randall et al., J. Med. Chem., 22, pp. 608–614 (1979).
G. S. Skinner et al., J. Am. Chem. Soc., 73, pp. 2230–2233 (1951).
G. S. Skinner et al., J. Am. Chem. Soc., 70, pp. 4011–4013 (1948).

*Primary Examiner*—Donald G. Daus
*Assistant Examiner*—D. B. Springer
*Attorney, Agent, or Firm*—Raymond M. Speer; Michael C. Sudol, Jr.

[57] ABSTRACT

Novel 4-(substituted thiazolyl)-3-hydroxy-3-pyrroline-2,5-diones are disclosed which inhibit glycolic acid oxidase and thus are useful in the treatment and prevention of calcium oxalate renal lithiasis.

10 Claims, No Drawings

4-(SUBSTITUTED PHENYL THIAZOLYL)-3-HYDROXY-3-PYRROLINE-2,5-DIONES

BACKGROUND OF THE INVENTION

Close to 70% of kidney stones in man are composed partially or predominantly of calcium oxalate. There is no satisfactory drug specific for the treatment of calcium oxalate renal lithiasis, nor for prophylactic use by patients prone to recurrent attacks of this disease.

The most common treatment for renal lithiasis due to calcium oxalate consists of surgical removal of stones, control of the diet to restrict calcium or oxalate, and ingestion of large quantities of water to dilute the urine. Attempts at chemotherapy have included the administration of magnesium oxide, calcium carbimide, orthophosphate, cellulose phosphate, isocarboxazide, thiazide diuretics, allopurinol and succinimide. Limited success has been realized by these drug approaches. No drug which specifically inhibits the biosynthetic formation of oxalic acid has previously been developed for the treatment of calcium oxalate renal lithiasis.

The immediate metabolic precursor of the majority of the oxalate in the urine of a typical patient is glyoxylic acid. In turn its most important precursor is glycolic acid. The enzyme glycolate oxidase is able to carry out the oxidation of glycolic acid, through glyoxylic acid, to oxalic acid. Inhibition of this enzyme will, therefore, reduce the concentration of oxalic acid in the kidney and bladder, reducing the probability that calcium oxalate crystallization will occur. Thus inhibitors of glycolate oxidase provide a specific approach to the prevention and treatment of calcium oxalate renal lithiasis.

Liao, et al, *Arch. Biochem. Biophys.*, 154, 68–75 (1973) have shown that phenyllactic acid and n-heptanoic acid, which are inhibitors of glycolate oxidase, inhibit oxalate biosynthesis in isolated perfused rat liver. These compounds are not sufficiently potent to be useful as drugs.

The preparation of 3-hydroxy-4-phenyl-3-pyrroline-2,5-dione

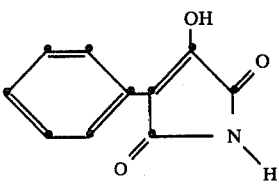

has been described by Harlay, *J. Pharm. Chim.*, 24, 537-48 (1936). 3-Hydroxy-4-aryl-3-pyrroline-2,5-diones are described in U.S. Pat. No. 3,349,263 as intermediates in the preparation of antiphlogistic substances.

A number of 3-hydroxy-4-substituted phenyl-3-pyrroline-2,5-diones are reported by G. S. Skinner, et al., *J. Am. Chem. Soc.*, 73, 2230 (1951). (In this paper these compounds are referred to as pyrrolidine-2,3,5-trione derivatives). 3-Hydroxy-4-(4-bromo-1-naphthyl)-3-pyrroline-2,5-dione is described by G. S. Skinner, et al., *J. Am. Chem. Soc.*, 70, 4011 (1948).

SUMMARY OF THE INVENTION

It has now been found that novel compounds of the formula:

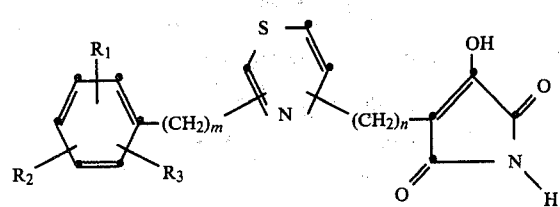

wherein
n is 0 to 2;
m is 0 to 3;
$R_1$, $R_2$ and $R_3$ are independently hydrogen, halogen, loweralkyl containing 1 to 6 carbons, trifluoromethyl, loweralkoxy containing 1 to 6 carbons or pharmaceutically acceptable salts thereof, with the proviso that the substituents on the thiazolyl ring are not adjacent, are potent inhibitors of glycolate oxidase. They are, therefore, useful in the treatment and prevention of calcium oxalate kidney and bladder stone disease.

Preferred compounds are those
wherein
n is 0;
m is 0;
having the structure:

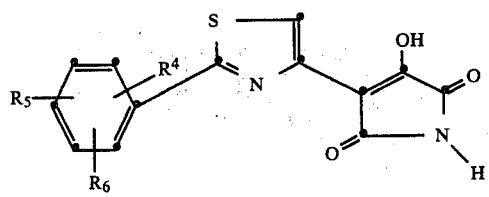

wherein
$R_4$, $R_5$ and $R_6$ are independently hydrogen, halogen, loweralkyl containing 1 to 6 carbon atoms, loweralkoxy containing 1 to 6 carbon atoms, and pharmaceutically acceptable salts thereof.

Further preferred compounds are those
wherein
$R_4$ is loweralkoxy containing 1 to 3 carbon atoms;
$R_5$ and $R_6$ are chlorine or compounds wherein
$R_4$ is hydrogen;
$R_5$ and $R_6$ are chlorine; or compounds wherein
$R_4$ and $R_5$ are hydrogen;
$R_6$ is bromine and pharmaceutically acceptable salts thereof.

Still further preferred specific compounds are:

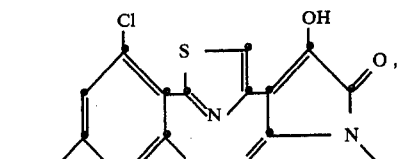

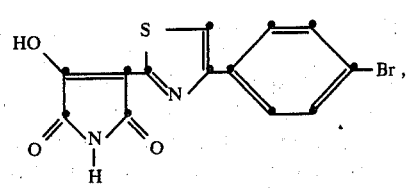

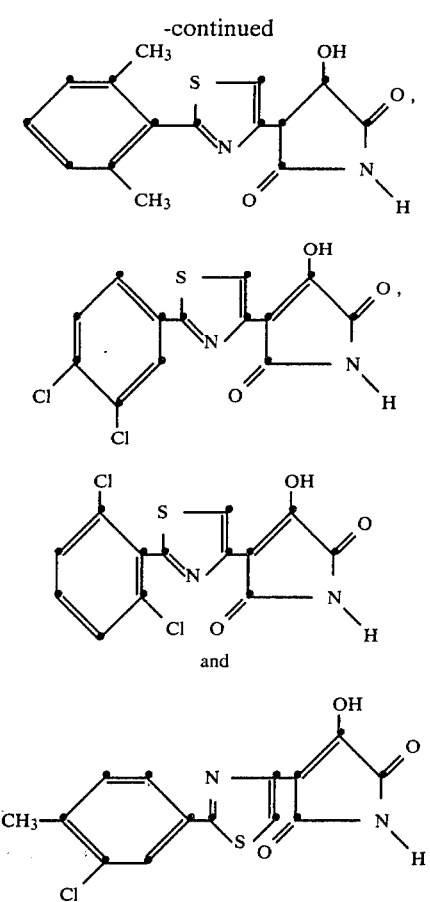

and pharmaceutically acceptable salts thereof.

DETAILED DESCRIPTION

About 70% of all renal calculi contain oxalate as the main component of the matrix. In the majority of patients the condition is associated with a higher than average level of metabolically produced oxalate. The major pathway for biosynthesis of oxalate can be represented as follows:

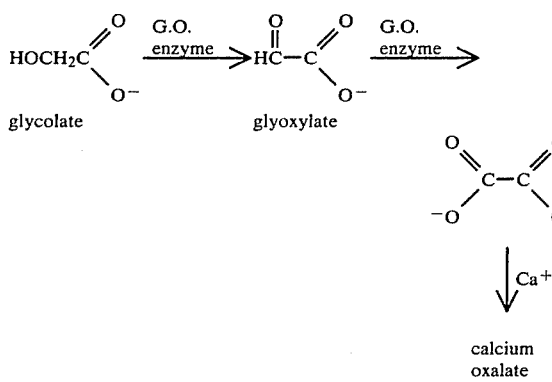

Glyoxylate is the major immediate forerunner of oxalate. An inhibitor of glycolate oxidase (G.O.) will inhibit both the conversion of glyoxylate to oxalate as well as the production of glyoxylate from glycolate. By reducing oxalic acid levels in the urine with the compounds of this invention, the formation of oxalate calculi will be reduced or prevented.

Compounds of formula (I) are potent inhibitors of glycolate oxidase and thus are useful in restricting oxalate levels in the blood and urine. Further, they are useful in the treatment and prevention of renal disease due to calcium oxalate stone formation in the kidney and bladder. They may be useful in the treatment of the genetically inherited diseases termed Hyperoxaluria types I and II in which very high levels of metabolic oxalic acid are present.

Compounds of formula (I) have been unexpectedly found to block the contractions of guinea pig ileum induced by Slow Reacting Substance of Anaphylaxis (SRS-A). They are ineffective against contractions caused by histamine, which demonstrates specificity against SRS-A. SRS-A is considered a major mediator in human allergic asthma. Thus the compounds of formula (I) are useful in the treatment of allergy, especially allergic asthma.

Compounds of formula (I) can be prepared according to the following schemes:

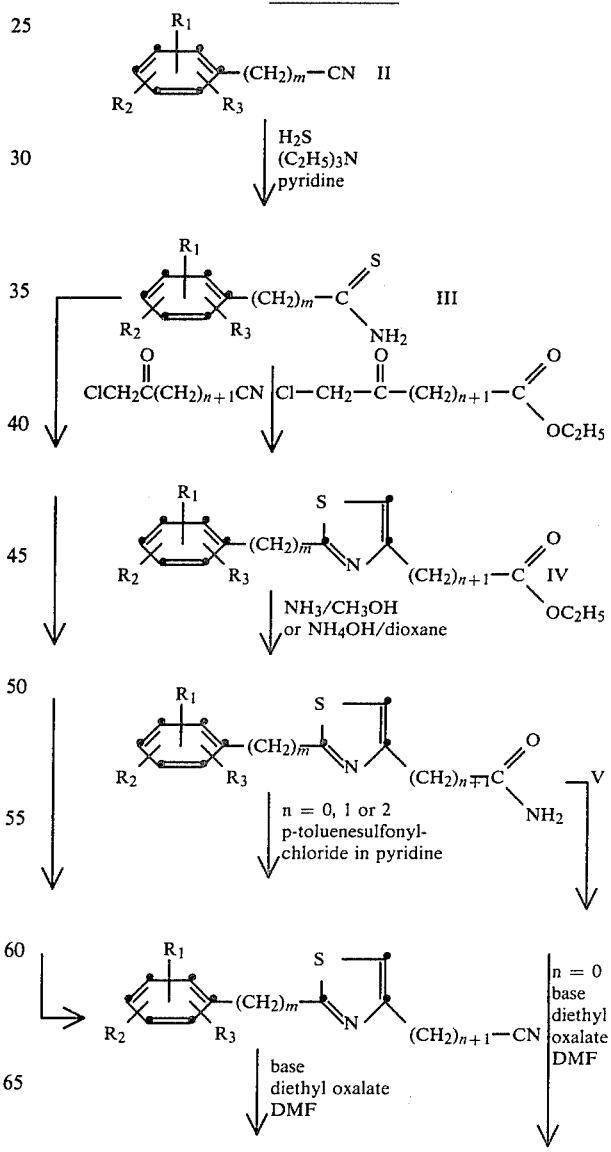

4,298,743

-continued
SCHEME 1

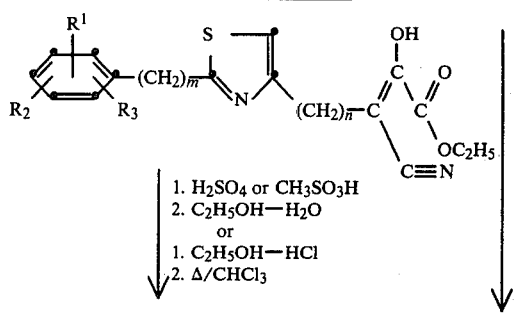

1. $H_2SO_4$ or $CH_3SO_3H$
2. $C_2H_5OH$—$H_2O$ or

1. $C_2H_5OH$—HCl
2. $\Delta$/$CHCl_3$

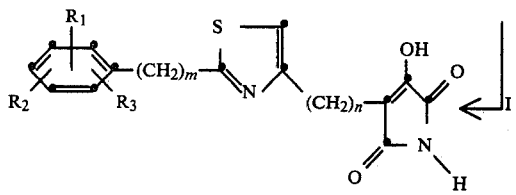

SCHEME 2

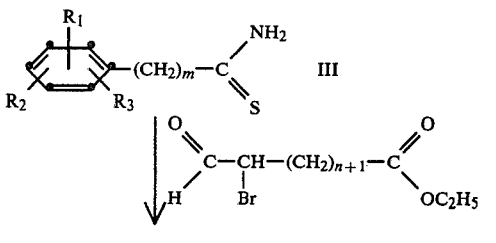  III

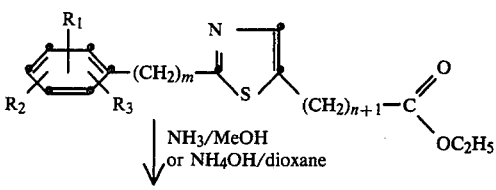

$NH_3$/MeOH
or $NH_4OH$/dioxane

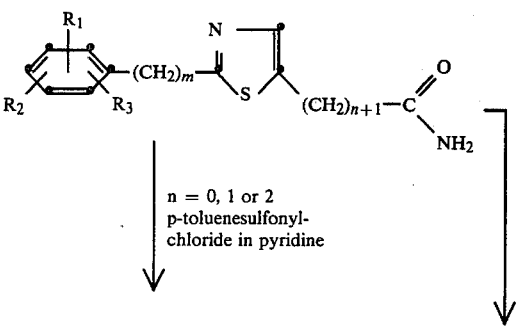

n = 0, 1 or 2
p-toluenesulfonyl-
chloride in pyridine

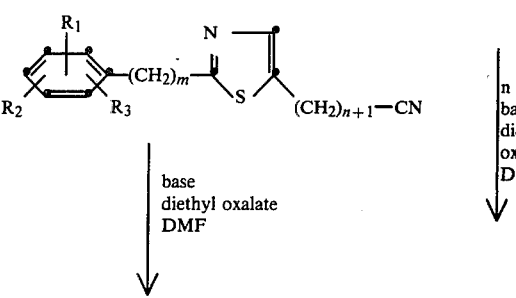

base
diethyl oxalate
DMF

-continued
SCHEME 2

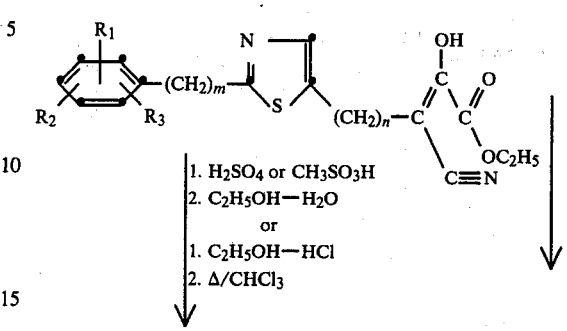

1. $H_2SO_4$ or $CH_3SO_3H$
2. $C_2H_5OH$—$H_2O$ or

1. $C_2H_5OH$—HCl
2. $\Delta$/$CHCl_3$

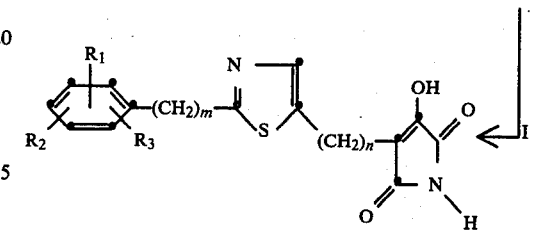

SCHEME 3

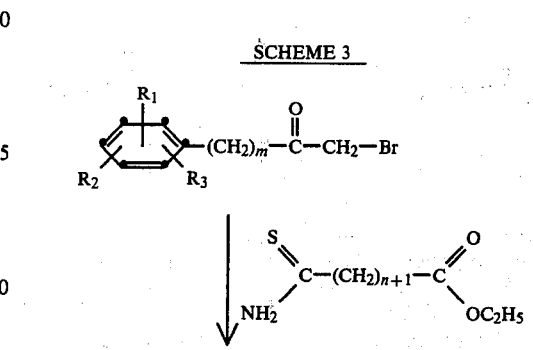

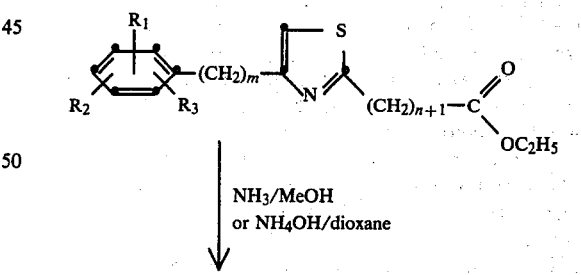

$NH_3$/MeOH
or $NH_4OH$/dioxane n = 0
base
diethyl oxalate
DMF

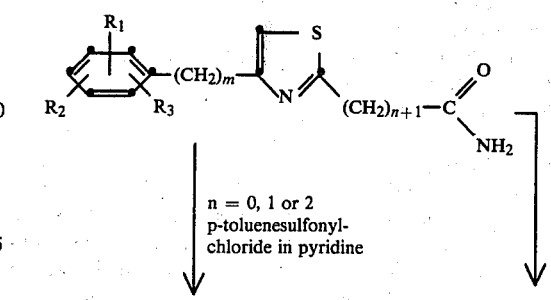

n = 0, 1 or 2
p-toluenesulfonyl-
chloride in pyridine

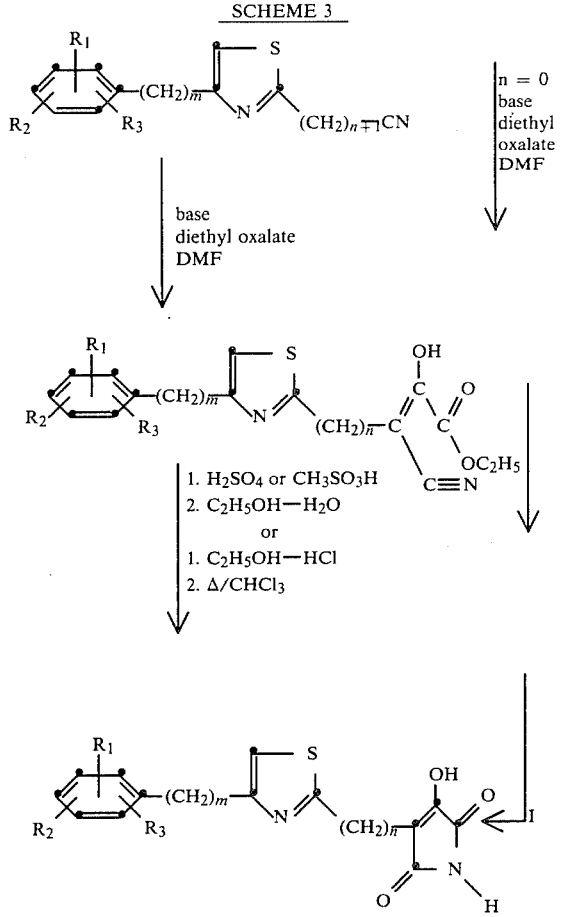

wherein m, $R_1$, $R_2$ and $R_3$ are as defined above.

The compounds (III) are prepared generally by the method of Fairfull, Lowe and Peak, *J. Chem. Soc.*, 742 (1952). The nitrile (II), prepared by known methods, is reacted with an excess of hydrogen sulfide gas in the presence of excess triethylamine in a basic organic solvent such as pyridine. When the reaction is complete, the reaction mixture is poured into ice-water and the thiobenzamide (III) collected by filtration.

The thioazole rings (IV) are assembled by the classic Hantzsch procedure using the thioamide (III) and ethyl 4-chloroacetoacetate or its homologs.

Stirring the esters (IV) in concentrated ammonium hydroxide and dioxane, or in methanol saturated with ammonia, for varying lengths of time yield the corresponding amides (V).

Preparation of the pyrrolinediones from the amides (V) is accomplished by reacting (V) with diethyl oxalate in DMF with strong base such as potassium t-butoxide or sodium ethoxide under an inert atmosphere. The reaction can also be carried out in alcoholic solvents such as methanol, ethanol and isopropanol with the corresponding alkoxides as base.

For compound of this invention where n=0, 1 or 2, 5-bromolevulinic acid ethyl ester and 6-bromo-5-oxohexanoic acid ethyl ester, respectively, are utilized in the thiazole forming step (in place of ethyl 4-chloroacetoacetate). After conversion to the amide, dehydration to the nitrile is carried out by standard methods well known in the art (e.g., with p-toluenesulfonyl chloride in pyridine or thionyl chloride in DMF). An alternative route to the nitrile intermediate involves reaction of the thioamide directly with the appropriate halomethylketone-substituted alkyl cyanide (e.g., 6-chloro-5-oxohexanenitrile can be utilized to form the nitrile intermediate where n+1=3). Reaction of the nitrile with diethyl oxalate in the presence of base (usually sodium or potassium alkoxide in solvents such as methanol, ethanol, dimethylformamide, or toluene at room temperature to 60° C.) provides the intermediate 3-cyano-2-keto acid ester. Cyclization to the hydroxypyrrolinedione (I) is carried out by reaction first in strong acid, such as sulfuric or methanesulfonic acid for several hours to overnight, and then mixing the solution with ethanol containing 5–10% water. Evaporation of the ethanol and extraction with chloroform or ethyl acetate provides the desired 3-hydroxy-3-pyrroline-2,5-dione product. The sulfuric or methanesulfonic acid solutions may be quenched with ice-water. Alternatively, the nitrile intermediate may be first converted to the imino ether with cold HCl in ethanol. The imino ether, when heated in chloroform, is converted to the hydroxypyrrolinedione (I).

For derivatives of (I) prepared by Scheme 2 where the aryl or aralkyl substituent is attached through the 2-position of the thiazole ring, while the hydroxypyrrolinedione moiety is attached through the 5-position of the thiazole ring, the thiazole-forming reaction employs a different α-halocarbonyl reagent. In place of the 4-chloroacetoacetic acid ethyl ester and its higher homologs, there are utilized the isomeric α-haloaldehydic alkanoic acid ester reagents (e.g.,

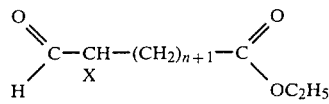

wherein X is halogen).

For example, in place of 4-chloroacetoacetic acid diethyl ester, one uses 4-oxo-3-bromobutyric acid ethyl ester. Other steps and reacting conditions are the same as described above.

For derivatives of (I) where the aryl or aralkyl substituent is in the 4-position of the thiazole ring and the hydroxypyrrolinedione moiety is converted through the 2-position of the thiazole ring, a slightly different route is followed as shown in Scheme 3. The starting material contributing the

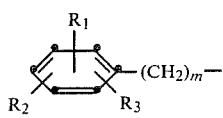

moiety is the corresponding halomethyl ketone,

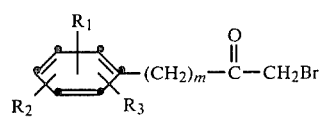

These are either known in the literature or are readily prepared from the acid chlorides

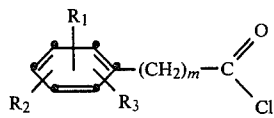

by reaction with diazomethane in diethyl ether to give the diazoketone intermediate

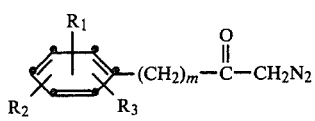

followed by reaction with hydrogen bromide in diethyl ether which generates the required bromomethylketone. The bromomethyl ketone intermediate is reacted with the appropriate ethoxycarbonylalkylthioamide

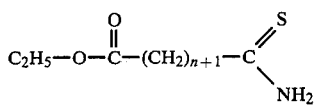

in refluxing ethanol to form the 4-substituted-2-thiazolylalkanoic acid ethyl ester which is converted to the amide and subsequently to the hydroxypyrrolinedione derivative by the procedures outlined above.

Included within the scope of the invention are the pharmaceutically acceptable salts of formula (I) compounds. The compounds of formula are strong organic acids with a pKa in the range 2-4. These salts are readily formed with the usual inorganic cations such as sodium, potassium and ammonium. Salts with organic amines such as trimethylamine, triethylamine, n-butylamine and the like are also very stable. The neutralization can be carried out by a variety of procedures known to the art to be generally useful for the preparation of such salts. The choice of the most suitable procedure will depend on a variety of factors including convenience of operation, economic considerations, and particularly the solubility characteristics of the particular free base, the acid, and the acid addition salt.

The compounds of formula (I) are utilized for the stated utilities by formulating them in a composition such as tablet, capsule or elixir for oral administration. Sterile solutions or suspensions can be used for parenteral administration. About 10 to 200 mg of a compound of formula (I) or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in the composition is such that dosage in the range indicated is obtained. The total daily dose will be in the 30 to 2000 mg range and preferably in the range of 50 mg. to 1000 mg.

Illustrative of the adjuvants which may be incorporated in tablets, capsules and the like are the following: a binder such as gum tragacanth, acacia, corn starch or gelatin; and excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain, in addition to materials of the above type, a liquid carrier such as a fatty oil. Various other materials may be present as coating or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a conventional vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples, given by way of illustration and not to be construed as limiting, further clarify the invention.

EXAMPLE 1

Preparation of p-Fluorothiobenzamide

Eighty-five ml of dry pyridine was saturated with hydrogen sulfide. To this was added 25 g of p-fluorobenzonitrile and 33 ml of triethylamine. Hydrogen sulfide was passed through the solution at room temperature, with good stirring. After 4 hours a sample on thin layer chromatography showed no nitrile. The solution was poured into water (600 ml) and ice. The solid product was filtered, washed with water and dried. Yield of 27.3 g, mp 143°—145° C.

EXAMPLE 2

Preparation of Ethyl 2-(3-Bromophenyl)-4-thiazolylacetate

3-Bromothiobenzamide (10.8 g) and ethyl 4-chloroacetoacetate (8.3 g) were dissolved in 50 ml of alcohol. The reaction was stirred and heated under reflux for 4 hours. When cooled, the crystalline solid was filtered yielding 12.2 g of product, mp 65°–70° C. When recrystallized from ether-petroleum ether, it melted 68°–70° C.

Anal. calc'd. for $C_{13}H_{12}BrNO_2S$. Calc'd.: N, 4.29; C, 47.86; H, 3.71. Found: N, 4.28; C, 48.07; H, 3.56.

EXAMPLE 2a

Preparation of Ethyl 2-(4-Bromophenyl)-thiazol-4-ylacetate

A mixture of 4-bromothiobenzamide (7.62 g, 35.2 mmole), ethyl 4-chloroacetoacetate (5.82 g, 35.2 mmole) and dimethylformamide (23 ml) was stirred under nitrogen and heated in an oil-bath at 115°–120° C. for 1½ hours. Thin layer chromatography showed the presence of unreacted thioamide. More ethyl chloroacetoacetate (2.91 g, 17.6 mmole) was added and heating was continued for 1½ hours, by which time no unreacted thioamide remained. The mixture was cooled and poured into ice-water (125 ml) and extracted with ether (2×100 ml). The extract was washed with water (2×100 ml), dried (MgSO₄) and evaporated to a semi-solid which contained the desired ester and the corresponding acid. The mixture was dissolved in ethanol (100 ml) saturated with hydrogen chloride and the solution was allowed to stand at room temperature for 1 day. The solution was evaporated to dryness and the ester was used without further purification for preparing the amide.

EXAMPLE 3

Preparation of 2-(3-Bromophenyl)-41-thiazolylacetamide

Ethyl 2-(3-bromophenyl)-4-thiazolylacetate prepared by the process in Example 2 (10 g) in 75 ml of 28% NH$_4$OH was stirred at room temperature. About 10 ml of dioxane was added to facilitate mixing. After 10 days, the crystalline product was filtered. The yield of product was 8.3 g, mp 150°–152° C. When recrystallized from alcohol, it melted 152°–154° C.

Anal. calc'd. for C$_{11}$H$_9$BrN$_2$OS. Calc'd.: N, 9.43; C, 44.46; L H, 3.05. Found: N, 9.45; C, 44.75; H, 2.97.

EXAMPLE 4

Preparation of 4-[2-(3-Bromophenyl)-4-thiazolyl]-3-hydroxy-3-pyrroline-2,5-dione The procedure for the preparation of the pyrrolinediones as set forth in Example 6 below gave the title compound, mp 258°–261° C. when 3-bromobenzonitrile was employed as the starting nitrile, and the conditions of Examples 1, 2 and 3 utilized for its conversion to 2-[2-(3-bromophenyl)thiazol-4-yl]acetamide.

EXAMPLE 5

Preparation of 4-(4-Bromophenyl)-2-thiazolylacetic Acid Ethyl Ester

A mixture of p-α-dibromoacetophenone (13.9 g, 0.05 mole) and 2-thiocarbamoylacetic acid ethyl ester in ethanol (65 ml) was heated under reflux for 2½ hours. On cooling, there was obtained the title compound (12.2 g) mp 189°–191° C. (dec). An analytical sample recrystallization from ethanol had mp 191°–193° C.

Analysis Calc. for C$_{13}$H$_{13}$Br$_2$NO$_2$S. Calc.: C, 38.35; H, 3.22; N, 3.44; Br, 39.25. Found: C, 38.07; H, 2.95; L N, 3.48; Br, 39.15.

EXAMPLE 6

General Method for the Preparation of 3-Hydroxy-4-substituted-3-pyrroline-2,5-diones Where n=0

A mixture of the substituted acetamide (10 mmole), diethyl oxalate (1.533 g, 10.5 mmole) and dry dimethylformamide (20 ml) is stirred under nitrogen or argon and cooled in an ice-bath. Potassium t-butoxide (2.464 g, 22 mmole) is added in two equal portions 15 minutes apart and the reaction mixture is stirred for about 30 minutes in the ice-bath and then at room temperature overnight. The reaction mixture is poured into ice-water (100 ml). If the potassium salt of the product dissolves, the aqueous mixture is extracted with ethyl acetate (2×35 ml) and then acidified with 6 N hydrochloric acid in order to precipitate the product. The product is either collected by filtration or by extraction with ethyl acetate.

If the potassium salt is not soluble when the reaction mixture is quenched in ice-water, then it is necessary to acidify the resulting suspension and collect the product by filtration. The crude product is generally less pure when obtained in this way.

If the compounds are solvated after recrystallization (with either DMF, dioxane, isopropanol or acetonitrile) drying at 110° C./0.05 Torr in order to remove the solvate may be required.

EXAMPLE 7

4-[2-(4-Bromophenyl)-5-thiazolyl]-3-hydroxy-3-pyrroline-2,5-dione

A mixture of 4-bromothiobenzamide (2.16 g., 0.01 mole) and ethyl 3-bromo-4-oxobutyrate (3.2 g., 0.015 mole) in ethanol (50 ml.) is heated at reflux for 6 hours. On cooling and partial evaporation there is obtained 2-(4-bromophenyl)thiazol-5-ylacetic acid ethyl ester. Reaction of this product with ammonia according to the procedure of Example 3 gives 2-(4-bromophenyl)-thiazol-5-ylacetamide, which on reaction with diethyl oxalate and base in dimethylformamide, according to the general procedure of Example 6, affords the title compound.

EXAMPLE 8

3-Hydroxy-4-[[2-(4-bromophenyl)-4-thiazolyl]ethyl]-3-pyrroline-2,5-dione

A mixture of 4-bromothiobenzamide (2.16 g., 0.01 mole) and 6-chloro-5-oxohexanenitrile (2.28 g., 0.012 mole) is heated at 60° C. in toluene for 12 hours. On cooling and partial evaporation, there is obtained 3-[2-(4-bromophenyl)thiazol-4-yl]butanenitrile.

To 3-[2-(4-bromobiphenyl)thiazol-4-yl]butanenitrile (3.07 g., 0.01 mole) in dimethylformamide (30 ml.) is added diethyloxalate (1.74 g., 0.012 mole) and potassium t-butoxide (2.48 g., 0.022 mole). The mixture is stirred overnight. Following evaporation under vacuum to one-half volume, chloroform (300 ml.) is added, plus water (200 ml.), and the mixture acidified with conc. HCl to pH 2-3. The chloroform is separated and washed well with water. The combined aqueous fractions are extracted a second time with chloroform. The combined chloroform extracts on evaporation provide 2-oxo-3-cyano-5-[2-(4-bromophenyl)thiazol-4-yl]-pentanoic acid ethyl ester. The ester (1.97 g., 0.005 mole) is dissolved in methanesulfonic acid (70 ml.) and stirred overnight. To the mixture is added 80% ethanol-water (200 ml.). After standing for two hours the ethanol is partially removed by evaporation to give the title compound.

EXAMPLE 9

2-[2-(3,4-Dichlorophenyl)thiazol-4-yl]acetonitrile

To 2-[2-(3,4-dichlorophenyl)thiazol-4-yl]-acetamide (2.87 g., 0.01 mole) in pyridine (30 ml.) is added gradually p-toluenesulfonyl chloride (1.91 g., 0.01 mole). After stirring for one hour, the mixture is poured into excess ice-water to give the title compound.

The following table contains physical properties of certain intermediates and end products of this invention. The Roman numerals refer to the numbered compounds in Scheme I previously described.

TABLE I

| | (IV) S-R=N with CH2CO2C2H5 | | (V) S-R=N with CH2CONH2 | | (I) S-R=N fused ring with OH | |
|---|---|---|---|---|---|---|
| RCN (II) | Calc. | Fd. | Calc. | Fd. | Calc. | Fd. |
| F—⌬—CN | N 5.28<br>C 58.85<br>H 4.56<br>BP/0.2 135–138° C.<br>MP 44–47° C. | 5.37<br>58.43<br>4.48 | N 11.86<br>C 55.92<br>H 3.84<br>MP 164–166° C. | 11.87<br>55.99<br>3.73 | N 9.65<br>C 53.79<br>H 2.43<br>MP 243–246° C. | 9.60<br>53.61<br>2.31 |
| Br—⌬—CN | N 4.29<br>C 47.86<br>H 3.71<br>MP 68–70° C.<br>As HCl Salt | 4.28<br>48.07<br>3.56 | N 9.43<br>C 44.46<br>H 3.05<br>MP 150–152° C. | 9.45<br>44.75<br>2.97 | N 7.98<br>C 44.46<br>H 2.01<br>MP 258–261° C. | 8.09<br>44.66<br>1.90 |
| Br—⌬—CH2CN | N 3.72<br>C 44.63<br>H 4.01<br>Cl 9.41<br>Br 21.21<br>MP 160–163° C. | 3.75<br>44.51<br>3.92<br>8.89<br>21.79 | N 9.00<br>C 46.31<br>H 3.56<br>MP 123–126° C. | 9.15<br>46.97<br>3.41 | N 7.62<br>C 46.04<br>H 2.48<br>MP 199–202° C. | 7.64<br>46.40<br>2.42 |
| CF3—⌬—CN | N 4.44<br>C 53.33<br>H 3.81<br>MP 68–69° C. | 4.60<br>53.23<br>3.66 | N 9.75<br>C 50.34<br>H 3.17<br>MP 160–162° C. | 9.69<br>50.33<br>3.16 | N 8.23<br>C 49.41<br>H 2.07<br>MP 262–264° C. | 8.41<br>49.48<br>2.11 |
| Br—⌬—CN | | | S 10.77<br>C 44.47<br>H 3.05<br>MP 181.5–182.5° C. | 10.81<br>44.64<br>3.21 | N 7.88<br>C 43.91<br>H 2.13<br>MP 273–274° C. (dec) | 7.80<br>43.85<br>1.94 |
| Cl—⌬—CN | N 4.97<br>C 55.41<br>H 4.29<br>MP 114–116° C. | 5.03<br>55.38<br>4.31 | N 11.09<br>C 52.28<br>H 3.59<br>MP 168–170° C. | 11.20<br>52.25<br>3.62 | N 9.14<br>C 50.90<br>H 2.30<br>MP 246–250° C. | 9.19<br>50.98<br>2.32 |
| CH3—⌬(Cl)—CN | N 4.74<br>C 56.85<br>H 4.77<br>MP 53–55° C. | 4.63<br>57.09<br>4.82 | N 10.50<br>C 54.03<br>H 4.16<br>MP 175–177° C. | 10.30<br>54.00<br>4.13 | N 8.74<br>C 52.42<br>H 2.83<br>MP 273–275° C. | 8.75<br>52.35<br>2.90 |
| 2,6-Cl2—⌬—CN | N 4.43<br>C 49.38<br>H 3.51<br>BP 184/0.2 | 4.47<br>49.27<br>3.48 | N 9.76<br>C 46.00<br>H 2.81<br>MP 128–130° C. | 9.64<br>45.85<br>2.76 | N 8.21<br>C 45.76<br>H 1.77<br>MP 244–246° C. | 8.25<br>45.65<br>1.72 |
| 3,4-Cl2—⌬—CN | N 4.43<br>C 49.38<br>H 3.51<br>MP 74–77° C. | 4.25<br>49.06<br>3.45 | N 9.76<br>C 46.00<br>H 2.81<br>MP 164–166° C. + 175–177° C. | 9.88<br>45.99<br>2.77 | N 8.21<br>C 45.76<br>H 1.77<br>MP 281–283° C. | 8.40<br>45.56<br>1.78 |
| 2,3-Cl2—⌬—CN | N 4.43<br>C 49.38<br>H 3.51<br>MP 68–70° C. | 4.28<br>48.96<br>3.52 | N 9.76<br>C 46.00<br>H 2.81<br>MP 153–154° C.<br>As HCl Salt | 9.72<br>45.81<br>2.84 | N 8.21<br>C 45.76<br>H 1.77<br>MP 291–293° C. | 8.49<br>45.60<br>1.81 |
| 2,6-(CH3)2—⌬—CN | N 4.49<br>C 57.77<br>H 5.82<br>MP 152–154° C. | 4.70<br>57.86<br>5.65 | | | N 9.33<br>C 59.98<br>H 4.29<br>MP 185–188° C. | 9.02<br>60.36<br>4.00 |
| CH3O—⌬(2,3-Cl2)—CN | N 4.06<br>C 48.70<br>H 3.79 | 4.05<br>48.83<br>3.92 | N 8.83<br>C 45.44<br>H 3.17 | 8.99<br>45.53<br>3.16 | N 7.55<br>C 45.30<br>H 2.17 | 7.63<br>45.38<br>2.14 |

TABLE I-continued

| | (IV) | | (V) | | *(I) |
|---|---|---|---|---|---|
| RCN (II) | R—thiazolyl-CH$_2$CO$_2$C$_2$H$_5$ | | R—thiazolyl-CH$_2$CONH$_2$ | | R—thiazolyl-pyrroline-dione |
| | Calc. | Fd. | Calc. | Fd. | Calc. | Fd. |
| | MP 76–78° C. | | MP 152–154° C. | | MP 275–276° C. |

*Note
The compounds of this invention may be designated 3-(Substituted thiazolyl)-4-hydroxy-3-pyrroline-2,5-dione derivatives.
Compounds (IV) prepared by process of Example 2 or Example 2a.
Compounds (V) prepared by process of Example 3.
Compounds (I) prepared by process of Example 6.

TABLE II

| Y—C(O)—CH$_2$—Br | C$_2$H$_5$—CO$_2$—CH$_2$-(thiazolyl-Y) | | NH$_2$—CO—CH$_2$-(thiazolyl-Y) | | HO-pyrroline-dione-(thiazolyl-Y) | |
|---|---|---|---|---|---|---|
| | Calc. | Fd. | Calc. | Fd. | Calc. | Fd. |
| Br—C$_6$H$_4$—C(O)—CH$_2$—Br | C 38.35 | 38.07 | C 44.46 | 44.43 | C 44.46 | 44.82 |
| | H 3.22 | 2.95 | H 3.05 | 2.98 | H 2.01 | 1.99 |
| | N 3.44 | 3.48 | N 9.43 | 9.34 | N 7.98 | 7.93 |
| | Br 39.25 | 39.15 | | | | |
| | mp 191–193° C. | | mp 166–168° C. | | mp >310° C. | |

Compounds in Table II prepared by process of Scheme 3.

What is claimed is:

1. Compounds having the structure

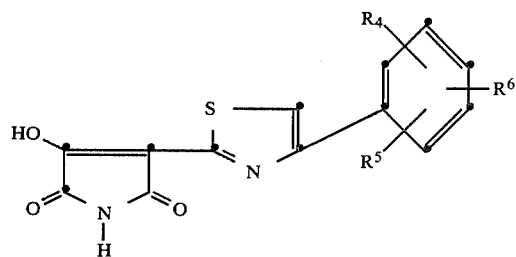

wherein
R$_4$, R$_5$ and R$_6$ are independently hydrogen, halogen, straight chained loweralkyl having 1 to 3 carbon atoms, loweralkoxy having 1 to 3 carbon atoms and the pharmaceutically acceptable salts thereof.

2. Compounds having the structure:

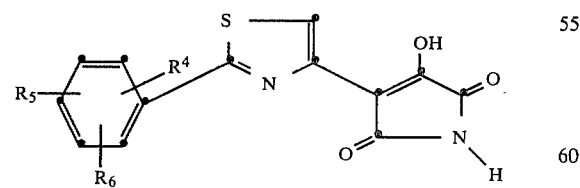

wherein
R$_4$, R$_5$ and R$_6$ are independently hydrogen, halogen, straight chained loweralkyl having 1 to 3 carbon atoms, loweralkoxy having 1 to 3 carbon atoms and pharmaceutically acceptable salts thereof.

3. The compounds according to claim 2 wherein R$_4$ is loweralkoxy having 1 to 3 carbon atoms;
R$_5$ and R$_6$ are chlorine and pharmaceutically acceptable salts thereof.

4. The compounds according to claim 2 wherein R$_4$ is hydrogen;
R$_5$ and R$_6$ are chlorine and pharmaceutically acceptable salts thereof.

5. The compounds according to claim 1 where R$_4$ and R$_5$ are hydrogen and R$_6$ is bromine.

6. The compound according to claim 3 having the structure:

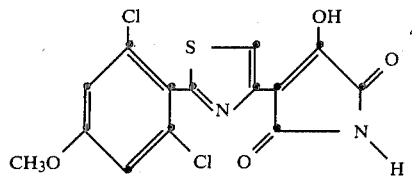

and pharmaceutically acceptable salts thereof.

7. The compound according to claim 4 having the structure:

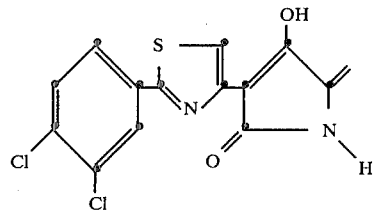

and pharmaceutically acceptable salts thereof.

8. The compound according to claim 4 having the structure:
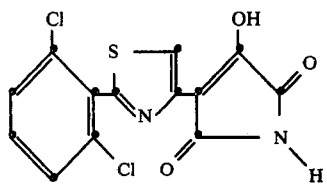
and pharmaceutically acceptable salts thereof.
9. The compound according to claim 2 having the structure:
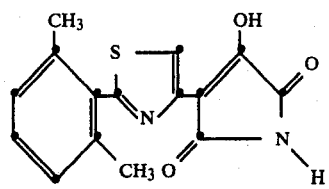
and pharmaceutically acceptable salts thereof.
10. The compound according to claim 1 having the structure:
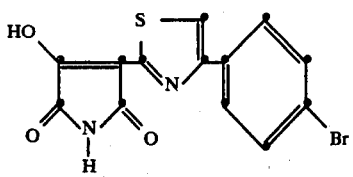
* * * * *